United States Patent
Dennis et al.

(10) Patent No.: US 6,638,537 B2
(45) Date of Patent: *Oct. 28, 2003

(54) MICROEMULSION AND MICELLE SYSTEMS FOR SOLUBILIZING DRUGS

(75) Inventors: Donn M. Dennis, Gainesville, FL (US); Nikolaus Gravenstein, Gainesville, FL (US); Jerome H. Modell, Gainesville, FL (US); Timothy E. Morey, Gainesville, FL (US); Dinesh Shah, Gainesville, FL (US)

(73) Assignee: University of Florida, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/924,290

(22) Filed: Aug. 8, 2001

(65) Prior Publication Data
US 2002/0120015 A1 Aug. 29, 2002

Related U.S. Application Data

(63) Continuation-in-part of application No. 09/630,237, filed on Aug. 1, 2000.

(51) Int. Cl.[7] ................................. A61K 9/50
(52) U.S. Cl. ............... 424/502; 424/400; 424/484; 424/486; 424/489; 424/501; 424/500
(58) Field of Search ................. 424/455, 400, 424/484, 486, 489, 501, 502, 500; 514/772, 772.1

(56) References Cited

U.S. PATENT DOCUMENTS

| | | |
|---|---|---|
| 5,478,860 A | 12/1995 | Wheeler |
| 5,560,931 A | 10/1996 | Eickhoff |
| 5,637,625 A | 6/1997 | Haynes |
| 5,726,164 A | 3/1998 | Weder |
| 5,750,142 A | 5/1998 | Friedman ..................... 424/450 |
| 5,858,410 A | 1/1999 | Muller |
| 5,908,619 A | 6/1999 | Scholz |
| 5,908,825 A | 6/1999 | Fasano et al. |
| 5,908,869 A | 6/1999 | Jones |
| 5,916,596 A | 6/1999 | Desai |
| 5,925,684 A | 7/1999 | Schweikert ................. 574/941 |
| 5,952,004 A * | 9/1999 | Rudnic et al. ............... 424/455 |
| 6,197,323 B1 * | 3/2001 | Georgieff ..................... 424/423 |
| 6,451,339 B2 * | 9/2002 | Patel et al. ................... 424/451 |

FOREIGN PATENT DOCUMENTS

| | | |
|---|---|---|
| WO | PCTUS93/09916 | 4/1994 |
| WO | PCT/IB96/00868 | 3/1997 |

* cited by examiner

Primary Examiner—Thurman K. Page
Assistant Examiner—Liliana Di Nola-Baron
(74) Attorney, Agent, or Firm—Brinks Hofer Gilson & Lione (57) ABSTRACT

A microemulsion delivery system for water insoluble or sparingly water soluble drugs that comprises a long polymer chain surfactant component and a short fatty acid surfactant component, with the amount of each being selected to provide stable microemulsion or micellar systems.

20 Claims, 2 Drawing Sheets

MICROEMULSION AND MICELLE SYSTEMS FOR SOLUBILIZING DRUGS

CROSS REFERENCED TO A RELATED APPLICATION

This application is a continuation-in-part of Dennis et al., Ser. No. 09/630,237 filed Aug. 1, 2000.

FIELD OF THE INVENTION

This invention relates to compositions and a method for making microemulsion delivery systems for water insoluble or sparingly soluble drugs.

BACKGROUND OF THE INVENTION

Dissolving water insoluble agents into aqueous solutions appropriate for human use (e.g., oral, topical application, intravenous injection, intramuscular injection, subcutaneous injection) represents a major technological hurdle for pharmaceutical delivery systems. Previous attempts have resulted in a number of serious side effects caused not by the drugs, but by the carrier agents used to dissolve the drug. These complications include significant hypotension during intravenous injection (e.g., amiodarone), painful injection with subsequent phlebitis (e.g., valium), anaphylaxis (e.g., propofol in Cremaphor), postoperative infections (e.g., propofol in Intralipid), and others. Clearly, an approach aimed at improving the solubilization of these drugs and avoiding the complications of solubilizing agents would enhance the quality of health care to patients. For many drugs, a major technological barrier for their routine clinical use is very poor solubility in the aqueous phase. For such drugs, oil/water macroemulsions have been commonly used in the pharmaceutical industry to "dissolve" a drug to its desired concentration. For example, the anesthetic propofol is supplied to the health care industry as Baxter PPI propofol (Gensia Sicor, Inc.) or Diprivan (AstraZeneca Pharmaceuticals, Inc.), as a macroemulsion of propofol in soybean oil (100 mg/mL), glycerol (22.5 mg/mL), egg lecithin (12 mg/mL), and disodium edetate (0.005%) or metabisulfite; with sodium hydroxide to adjust pH to 7.0–8.5. However, the stability of such macroemulsions is relatively poor, and the oil and water components separate into distinct phases over time. In addition, the droplet size of the macroemulsion increases with time. Macroemulsions are defined as formed by high shear mixing and normally having particles of 1 micron to 10 microns in size.

In contrast to macroemulsion systems, microemulsion systems consisting of oil, water, and appropriate emulsifiers can form spontaneously and are therefore thermodynamically stable. For this reason, microemulsion systems theoretically have an infinite shelf life under normal conditions in contrast to the limited life of macroemulsions (e.g., two years for Baxter PPI propofol). In addition, the size of the droplets in such microemulsions remains constant and ranges from 100–1000 angstroms (10–100 nm), and has very low oil/water interfacial tension. Because the droplet size is less than 25% of the wavelength of visible light, microemulsions are transparent. Three distinct microemulsion solubilization systems that can be used for drugs are as follows:

1. oil in water microemulsions wherein oil droplets are dispersed in the continuous aqueous phase;
2. water in oil microemulsions wherein water droplets are dispersed in the continuous oil phase;
3. bi-continuous microemulsions wherein microdomains of oil and water are interdispersed within the system. In all three types of microemulsions, the interface is stabilized by an appropriate combination of surfactants and/or co-surfactants.

It can be seen from the above description that there is a real and continuing need for the development of new and effective drug delivery systems for water insoluble or sparingly soluble drugs. One such approach might be pharmaceutical microemulsions. However, one must choose materials that are biocompatible, non-toxic, clinically acceptable, and use emulsifiers in an appropriate concentration range, and form stable microemulsions. This invention has as its objective the formation of safe and effective pharmaceutical microemulsion delivery systems.

The delivery system described herein has been found particularly useful for propofol, but is not exclusively limited thereto. It is presented here as an example of a state of the art drug, normally poorly soluble in its present delivery form, but when properly delivered in a pharmaceutical microemulsion carrier, the current problems can be solved. Such current problems in the case of propofol stem directly from its poor solubility in water. These include significant pain during injection, and post-operative infections in some patients who, for example, receive a macroemulsion of propofol for surgery or sedation.

In an attempt to lower health care costs, there has been an explosive growth in the number of surgical procedures being done on an outpatient basis in the United States. In the outpatient setting, the use of short acting anesthetics allows for prompt emergence from anesthesia and provides expeditious discharge of patients to their home. Propofol (2,6-diisopropylphenol, molecular weight 178.27) is an organic liquid similar to oil, has very little solubility in the aqueous phase (octanol/water partition coefficient 6761:1 at a pH 6.0–8.5), and is a short-acting intravenous anesthetic that meets the criteria of rapid anesthetic emergence with minimal side effects. Currently, propofol is supplied as a macroemulsion, an opaque dispersion using biocompatible emulsifiers such as phospholipids, cholesterol, and others. In addition, a number of other drawbacks cause significant limitations and risk to some patients.

Most of the disadvantages of propofol relate to its commercial formulation and physical properties. That is, propofol is a liquid at room temperature and is extremely insoluble in water. The inherent lipophilicity of propofol makes dissolution in saline or phosphate buffer problematic. In the early 1980's, Cremaphor was used as a solvent, but subsequently abandoned because of its propensity to cause life threatening anaphylactic reactions. Since that time, propofol is suspended in a macroemulsion consisting of 10% Intralipid, a milky white solution of soybean oil and other additives as specified previously. The current commercial formulation of propofol has several major disadvantages. First, use of propofol in Intralipid has been implicated as the causative agent contributing to several cases of postoperative infection in human patients as detailed by the Center for Disease Control and Prevention. The cause of the infections and death was attributed to extrinsically contaminated Diprivan (i.e., propofol in Intralipid) used as an anesthetic during the surgical procedures. To address the propensity of bacterial growth, manufacturers added the preservatives EDTA (0.05 mg/ml) to Diprivan and sodium metabisulfite (0.25 mg/ml) to Baxter PPI propofol. Unfortunately, both of these preservatives may potentially cause adverse reactions in humans. Whereas sodium metabisulfite may cause allergic-type reactions in susceptible patients, the chelating properties of EDTA were of concern to the FDA because of their effects on cardiac conduction and renal function. Thus, use of a solvent that does not support bacterial growth would significantly enhance the therapeutic safety of propofol not only by preventing intravenous injection of microbes, but also by obviating the need for preservatives and possible adverse effects of these agents.

Second, the cost of Intralipid substantially adds to the expense of manufacturing a propofol macroemulsion. This vehicle is produced by Clinitec, licensed to the pharmaceutical corporations for the purpose of solubilizing propofol, and constitutes a major fraction of the cost of producing Diprivan (propofol in 10% Intralipid).

A third major disadvantage of the current preparation of propofol relates to its free, aqueous concentrations. Propofol is a phenol derivative (2,6-diisopropylphenol) and causes pain on injection. This effect is the single greatest complaint of anesthesiologists and patients regarding propofol and may on occasion necessitate discontinuation of the drug for sedative purposes. Most authorities believe that the stinging relates to the concentration of propofol in free, aqueous solution.

A solvent that completely emulsifies or partitions propofol into the non-aqueous phase would preclude (or markedly reduce) stinging and allow painless injection similar to thiopental sodium (another widely used intravenous anesthetic). The formulations of the present invention address and overcome these three disadvantages.

SUMMARY OF THE INVENTION

A microemulsion delivery system for normally water insoluble or sparingly soluble drugs, such as propofol. The drug is microemulsified with an emulsifier combination of a long chain polymer surfactant component and a short chain fatty acid surfactant component. These are selected to reduce surface tension to absorption between the two phases to thereby allow the formation of thermodynamically stable microemulsions or micelles. The system is particularly useful for propofol, but is not limited to propofol.

DETAILED DESCRIPTION OF THE PREFERRED EMBODIMENTS

Microemulsion drug delivery systems of this invention are hereinafter described in conjunction with microemulsions with the pharmaceutically active anesthetic propofol. However, it should be understood that the use of propofol as the active water insoluble or sparingly soluble drug in the description is exemplary only of the generally described class of normally poorly water soluble drugs. Microemulsion systems of the present invention, particularly oil and water, can be used to dissolve substantial concentrations of oil-soluble drugs such as propofol, and they can thereafter be injected intravenously into human patients or animals with less, or even without pain caused by the delivery system.

Many water soluble drugs such as cyclosporine, insulin, and others can be dissolved in water-in-oil microemulsions and can be taken orally (e.g., gelatin capsule) or injected. These microemulsions spread over the intestinal surface wherein nanometer-sized water droplets with drugs dissolved therein permeate and diffuse across the intestinal brush border. The delivery of various drugs (i.e., oil-soluble, water-soluble, and interphase soluble drugs) in patients using the previously-mentioned three types of microemulsion systems consisting of biocompatible surfactants and co-surfactants will work. Such solutions can be especially valuable to patients with abdominal disorders that inhibit absorption such as short gut syndrome and for better oral delivery of expensive drugs that are otherwise poorly absorbed.

Substantially water insoluble pharmacologically active agents contemplated for use in the practice of the present invention include pharmaceutically active agents, not limited in class, except to say they are normally difficultly soluble in aqueous systems. Examples of pharmaceutically active drug agents include:

analgesics/antipyretics (e.g., aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, oxycodone hydrochloride, codeine phosphate, dihydrocodeine bitartrate, pentazocine hydrochloride, hydrocodone bitartrate, levorphanol tartrate, diflunisal, trolamine salicylate, nalbuphine hydrochloride, mefenamic acid, butorphanol tartrate, choline salicylate, butalbital, phenyltoloxamine citrate, diphenhydramine citrate, methotrimeprazine, cinnamedrine hydrochloride, meprobamate, and the like);

anesthetics (e.g., halothane, isoflurane, methoxyflurane, propofol, thiobarbiturates, xenon and the like);

antiasthmatics (e.g., Azelastine, Ketotifen, Traxanox, and the like);

antibiotics (e.g., neomycin, streptomycin, chloramphenicol, cephalosporin, ampicillin, penicillin, tetracycline, and the like);

antidepressants (e.g., nefopam, oxypertine, doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluoxetine hydrochloride, doxepin hydrochloride, imipramine hydrochloride, imipramine pamoate, nortriptyline, amitriptyline hydrochloride, isocarboxazid, desipramine hydrochloride, trimipramine maleate, protriptyline hydrochloride, and the like);

antidiabetics (e.g., biguanides, hormones, sulfonylurea derivatives, and the like);

antifungal agents (e.g., griseofulvin, keoconazole, amphotericin B, Nystatin, candicidin, and the like); antihypertensive agents (e.g., propanolol, propafenone, oxyprenolol, nifedipine, reserpine, trimethaphan camsylate, phenoxybenzamine hydrochloride, pargyline hydrochloride, deserpidine, diazoxide, guanethidine monosulfate, minoxidil, rescinamine, sodium nitroprusside, rauwolfia serpentina, alseroxylon, phentolamine mesylate, reserpine, and the like);

anti-inflammatories (e.g., (non-steroidal) indomethacin, naproxen, ibuprofen, ramifenazone, piroxicam, (steroidal) cortisone, dexamethasone, fluazacort, hydrocortisone, prednisolone, prednisone, and the like);

antineoplastics (e.g., adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, and the like);

antianxiety agents (e.g., lorazepam, buspirone hydrochloride, prazepam, chlordiazepoxide hydrochloride, oxazepam, clorazepate dipotassium, diazepam, hydroxyzine pamoate, hydroxyzine hydrochloride, alprazolam, droperidol, halazepam, chlormezanone, dantrolene, and the like);

immunosuppressive agents (e.g., cyclosporine, azathioprine, mizoribine, FK506 (tacrolimus), and the like); antimigraine agents (e.g., ergotamine tartrate, propanolol hydrochloride, isomeheptene mucate, dichloralphenazone, and the like);

sedatives/hypnotics (e.g., barbiturates (e.g., pentobarbital, pentobarbital sodium, secobarbital sodium), benzodiazapines (e.g., flurazepam hydrochloride, triazolam, tomazeparm, midazolam hydrochloride, and the like);

antianginal agents (e.g., beta-adrenergic blockers, calcium channel blockers (e.g., nifedipine, diltiazem hydrochloride, and the like), nitrates (e.g., nitroglycerin, isosorbide dinitrate, pentaerythritol tetranitrate, erythrityl tetranitrate, and the like));

antipsychotic agents (e.g., haloperidol, loxapine succinate, loxapine hydrochloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, and the like);

antimanic agents (e.g., lithium carbonate);

antiarrhythmics (e.g., amiodarone, related derivatives of amiodarone, bretylium tosylate, esmolol hydrochloride, verapamil hydrochloride, encainide hydrochloride, digoxin, digitoxin, mexiletine hydrochloride, disopyramide phosphate, procainamide hydrochloride, quinidine sulfate, quinidine gluconate, quinidine polygalacturonate, flecainide acetate, tocainide hydrochloride, lidocaine hydrochloride, and the like);

antiarthritic agents (e.g., phenylbutazone, sulindac, penicillamine, salsalate, piroxicam, azathioprine, indomethacin, meclofenamate sodium, gold sodium thiomalate, ketoprofen, auranofin, aurothioglucose, tolmetin sodium, and the like);

antigout agents (e.g., colchicine, allopurinol, and the like);

anticoagulants (e.g., heparin, heparin sodium, warfarin sodium, and the like);

thrombolytic agents (e.g., urokinase, streptokinase, altoplase, and the like);

antifibrinolytic agents (e.g., aminocaproic acid);

hemorheologic agents (e.g., pentoxifylline);

antiplatelet agents (e.g., aspirin, empirin, ascriptin, and the like);

anticonvulsants (e.g., valproic acid, divalproate sodium, phenytoin, phenytoin sodium, clonazepam, primidone, phenobarbitol, phenobarbitol sodium, carbamazepine, amobarbital sodium, methsuximide, metharbital, mephobarbital, mephenytoin, phensuximide, paramethadione, ethotoin, phenacemide, secobarbitol sodium, clorazepate dipotassium, trimethadione, and the like);

antiparkinson agents (e.g., ethosuximide, and the like);

antihistamines/antipruritics (e.g., hydroxyzine hydrochloride, diphenhydramine hydrochloride, chlorpheniramine maleate, brompheniramine maleate, cyproheptadine hydrochloride, terfenadine, clemastine fumarate, triprolidine hydrochloride, carbinoxamine maleate, diphenylpyraline hydrochloride, phenindamine tartrate, azatadine maleate, tripelennamine hydrochloride, dexchlorpheniramine maleate, methdilazine hydrochloride, trimprazine tartrate and the like);

agents useful for calcium regulation (e.g., calcitonin, parathyroid hormone, and the like);

antibacterial agents (e.g., amikacin sulfate, aztreonam, chloramphenicol, chloramphenicol palmitate, chloramphenicol sodium succinate, ciprofloxacin hydrochloride, clindamycin hydrochloride, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, colistin sulfate, and the like);

antiviral agents (e.g., interferon gamma, zidovudine, amantadine hydrochloride, ribavirin, acyclovir, and the like);

antimicrobials (e.g., cephalosporins (e.g., cefazolin sodium, cephradine, cefaclor, cephapirin sodium, ceftizoxime sodium, cefoperazone sodium, cefotetan disodium, cefutoxime azotil, cefotaxime sodium, cefadroxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium, and the like), prythronycins, penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G potassium, penicillin G procaine, methicillin sodium, nafcillin sodium, and the like), erythromycins (e.g., erythromycin ethylsuccinate, erythromycin, erythromycin estolate, erythromycin lactobionate, erythromycin siearate, erythromycin ethylsuccinate, and the like), tetracyclines (e.g., tetracycline hydrochloride, doxycycline hyclate, minocycline hydrochloride, and the like), and the like);

anti-infectives (e.g., GM-CSF);

bronchodilators (e.g., sympathomimetics (e.g., epinephrine hydrochloride, metaproterenol sulfate, terbutaline sulfate, isoetharine, isoetharine mesylate, isoetharine hydrochloride, albuterol sulfate, albuterol, bitolterol, mesylate isoproterenol hydrochloride, terbutaline sulfate, epinephrine bitartrate, metaproterenol sulfate, epinephrine, epinephrine bitartrate), anticholinergic agents (e.g., ipratropium bromide), xanthines (e.g., aminophylline, dyphylline, metaproterenol sulfate, aminophylline), mast cell stabilizers (e.g., cromolyn sodium), inhalant corticosteroids (e.g., flurisolidebeclomethasone dipropionate, beclomethasone dipropionate monohydrate), salbutamol, beclomethasone dipropionate (BDP), ipratropium bromide, budesonide, ketotifen, salmeterol, xinafoate, terbutaline sulfate, triamcinolone, theophylline, nedocromil sodium, metaproterenol sulfate, albuterol, flunisolide, and the like);

hormones (e.g., androgens (e.g., danazol, testosterone cypionate, fluoxymesterone, ethyltostosterone, testosterone enanihate, methyltestosterone, fluoxymesterone, testosterone cypionate), estrogens (e.g., estradiol, estropipate, conjugated estrogens), progestins (e.g., methoxyprogesterone acetate, norethindrone acetate), corticosteroids (e.g., triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate methylprednisolone sodium succinate, hydrocortisone sodium succinate, methylprednisolone sodium succinate, triamcinolone hexacatonide, hydrocortisone, hydrocortisone cypionate, prednisolone, fluorocortisone acetate, paramethasone acetate, prednisolone tebutate, prednisolone acetate, prednisolone sodium phosphate, hydrocortisone sodium succinate, and the like), thyroid hormones (e.g., levothyroxine sodium) and the like), and the like;

hypoglycemic agents (e.g., human insulin, purified beef insulin, purified pork insulin, glyburide, chlorpropamide, glipizide, tolbutamide, tolazamide, and the like);

hypolipidemic agents (e.g., clofibrate, dextrothyroxine sodium, probucol, lovastatin, niacin, and the like);

proteins (e.g., DNase, alginase, superoxide dismutase, lipase, and the like);

nucleic acids (e.g., sense or anti-sense nucleic acids encoding any therapeutically useful protein, including any of the proteins described herein, and the like);

agents useful for erythropoiesis stimulation (e.g., erythropoietin);

antiulcer/antireflux agents (e.g., famotidine, cimetidine, ranitidine hydrochloride, and the like);

antinauseants/antiemetics (e.g., meclizine hydrochloride, nabilone, prochlorperazine, dimenhydrinate, promethazine hydrochloride, thiethylperazine, scopolamine, and the like);

oil-soluble vitamins (e.g., vitamins A, D, E, K, and the like);

as well as other drugs such as mitotane, visadine, halonitrosoureas, anthrocyclines, ellipticine, and the like.

As well, the microemulsion systems of the present invention may be used in brain chemotherapy and gene chemotherapy, since the nature of the surface of virus particles is an important determinant of the transfer rate of viruses across the blood/brain barrier or into another protected compartment (e.g., intraocular cerebrospinal fluid).

Likewise, many chemotherapeutic agents dissolved in an oil in water microemulsion might be more readily delivered to a tumor site in the brain. For example, pediatric patients with brain tumors may frequently require general anesthesia so that chemotherapeutic agents can be safely injected into the cerebrospinal fluid by puncture of the lumbar cistern. Use of microemulsions to target brain tumors might obviate the need for anesthesia and/or lumbar puncture in adult and pediatric patients.

The solubility of nonpolar drugs can be significantly increased if dissolved in mixed solvents such as water and alcohol or propylene glycol by influencing the hydrophobic forces existing in the system. This approach will also be compared with microemulsion and selective micelle release systems. The mixed solvent system may be the simplest method to solve problems of drug solubilization.

In preparation of the pharmaceutically active drug such as propofol useful in highly bioavailable form in accordance with the present invention, the first step is to select the normally difficultly soluble drug, such as propofol, which is similar to an oil. In order to make a homogeneous microemulsion of the pharmaceutically active component such as propofol, one needs to mix it with the appropriate emulsifier combination for formation of the microemulsion.

Surprisingly, it has been found that in accordance with the present invention, the appropriate combination of surfactants is the combination of a long chain polymer surfactant component such as a poloxamer with a short chain fatty acid surfactant component. The ratio of long chain polymer surfactant to short chain fatty acid surfactant should be from 10 to 100, preferably from 25 to 80 (wt./wt.).

Suitable long chain surfactants can be selected from the group known as organic or inorganic surfactant pharmaceutical excipients. Preferred surfactants include nonionic and anionic surfactants.

Representative examples of long chain or high molecular weight (>1000) surfactants include gelatin, casein, lecithin (phosphatides), gum acacia, cholesterol, tragacanth, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, microcrystalline cellulose, magnesium aluminum silicate, triethanolamine, polyvinyl alcohol, and polyvinylpyrrolidene (PVP). The low molecular weight (<1000) include stearic acid, benzalkonium chloride, calcium stearate, glycerol monostearate, cetostearyl alcohol, cetomacrogol emulsifying wax, and sorbitan esters. Most of these surface modifiers are known pharmaceutical excipients and are described in detail in the Handbook of Pharmaceutical Excipients, published jointly by the American Pharmaceutical Association and The Pharmaceutical Society of Great Britain, the Pharmaceutical Press, 1986.

Particularly preferred long chain surfactants include polyvinylpyrrolidone, tyloxapol, poloxamers such as Pluronic F68, F77, and F108, which are block copolymers of ethylene oxide and propylene oxide, and polyxamines such as Tetronic 908 (also known as Poloxamine 908), which is a tetrafunctional block copolymer derived from sequential addition of propylene oxide and ethylene oxide to ethylenediamine, available from BASF, dextran, lecithin, dialkylesters of sodium sulfosuccinic acid, such as Aerosol OT, which is a dioctyl ester of sodium sulfosuccinic acid, available from American Cyanamid, Duponol P, which is a sodium lauryl sulfate, available from DuPont, Triton X-200, which is an alkyl aryl polyether sulfonate, available from Rohm and Haas, Tween 20 and Tween 80, which are polyoxyethylene sorbitan fatty acid esters, available from ICI Specialty Chemicals; Carbowax 3550 and 934, which are polyethylene glycols available from Union Carbide; Crodesta F-110, which is a mixture of sucrose stearate and sucrose distearate, available from Croda Inc., Crodesta SL-40, which is available from Croda, Inc., and SA9OHCO, which is $C_{18}H_{37}$-$CH_2$(CON($CH_3$)$CH_2$ (CHOH)$_4$ $CH_2$ OH)$_2$. Surface modifiers which have been found to be particularly useful include Tetronic 908, the Tweens, Pluronic F-68 and polyvinylpyrrolidone. Other useful surface modifiers include: decanoyl-N-methylglucamide; n-decyl.beta-D-glucsopyranoside; n-decyl.beta-D-maltopyranoside; n-dodecyl.beta-D-glucopyranoside; n-dodecyl.beta.-D-maltoside; heptanoyl-N-methylglucamide; n-heptyl-.beta.-D-glucopyranoside; n-heptyl.beta.-D-thioglucoside; n-hexyl.beta.-D-glucopyranoside; nonanoyl-N-methylglucamide; n-noyl.beta.-D-glucopyranoside; octanoyl-N-methylglucamide; n-octyl-.beta.-D-glucopyranoside; octyl.beta.-D-thioglucopyranoside; and the like.

Another useful long chain surfactant is tyloxapol (a nonionic liquid polymer of the alkyl aryl polyether alcohol type; also known as superinone or triton). This surfactant is commercially available and/or can be prepared by techniques known in the art.

Another preferred surfactant p-isononylphenoxypoly (glycidol) also known as Olin-10G or Surfactant 10-G, is commercially available as 10G from Olin Chemicals, Stamford, Conn.

One preferred long chain surfactant is a block copolymer linked to at least one anionic group. The polymers contain at least one, and preferably two, three, four or more anionic groups per molecule. Preferred anionic groups include sulfate, sulfonate, phosphonate, phosphate and carboxylate groups. The anionic groups are covalently attached to the nonionic block copolymer. The nonionic sulfated polymeric surfactant has a molecular weight of 1,000–50,000, preferably 2,000–40,000, and more preferably 3,000–30,000. In preferred embodiments, the polymer comprises at least about 50%, and more preferably, at least about 60% by weight of hydrophilic units, e.g., alkylene oxide units. The reason for this is that the presence of a major weight proportion of hydrophilic units confers aqueous solubility to the polymer.

A preferred class of block copolymers useful as surface modifiers herein includes block copolymers of ethylene oxide and propylene oxide. These block copolymers are commercially available as Pluronics. Specific examples of the block copolymers include F68, F77, F108 and F127.

Another preferred class of block copolymers useful herein include tetrafunctional block copolymers derived from sequential addition of ethylene oxide and propylene oxide to ethylene diamine. These polymers, in an unsulfated form, are commercially available as Tetronics.

To summarize, the long chain surfactant is preferably a block copolymer which is a poloxamer which is a copolymer of ethylene oxide and propylene oxide. These copolymers are commercially available as Pluronics®.

The second component of the co-surfactant or emulsifier combination is a short chain fatty acid component. By short chain is meant $C_8$ to $C_{16}$ chain length, preferably, $C_8$ to $C_{12}$. One preferred co-emulsifier with especially good results is sodium laurate.

The advantages of this combination system are that one can solubilize a broad range of concentrations of active drugs and optimize the exact composition of the microemulsion components. For example, with respect to propofol, high concentrations can be achieved if desired by using higher concentrations of the co-emulsifiers. Concentrations of propofol used by healthcare providers (i.e., 1% concentrate, 10 mg/mL) can be very easily achieved in the present system shown by Tables 1, 2, 3 and 4 with respect to the examples below. These are all clear solutions, colorless, thermodynamically stable over time (currently these have been demonstrated for stability up to at least 16 months), and do not support bacterial growth.

In addition to microemulsions, one can design the interface of such nanometer-sized droplets so that droplet stability and lifespan in humans can be selectively designed to last from a few milliseconds to minutes, or even to hours. We believe that the interfacial rigidity of the microemulsion droplets plays a key role in the flux of the drugs from such droplets to the cells and tissues. Tailoring of microemulsion systems to control the flux of the drugs can also be manipulated in such systems to customize drug delivery according to individual patient requirements or to specific pharmaceutical needs.

A mixture of one or more of the drug active ingredients in the microemulsion carrier composition of the present invention to generally lower the interfacial tension of the active ingredient to less than 0.1 duines/cm with a drop size of the active ingredient in the carrier liquid being preferably less than 200 nm. Preferably the combination that comprises the long chain polymer surfactant component in a short chain fatty acid surfactant component are selected so that they are safe to be taken by humans either orally or intravenously. In providing the composition for administration to humans intravenously and safely intravenously, the concentration would normally be less than 1000 mg of active material per one mL of total material. of course, the surfactant and the cosurfactant i.e. the long chain polymer surfactant active component and the short chain fatty acid surface active component are preferably selected from the GRAS list.

Drugs such as lidocaine and tetracaine can be obtained in base form (nonionic or unionized) or salt (ionic) form. The salt form of drugs has a much greater solubility in aqueous phase (i.e., water). For this reason, many drugs are commonly supplied in the salt form in the aqueous phase. We have shown that surface active drug molecules form micelles in the aqueous phase. These micelles can easily solubilize nonpolar or nonionic forms of drugs. Thus, we have shown that the solubility of a drug can be three to five-fold greater in the aqueous phase if we put ionized and unionized forms of lidocaine into the aqueous phase.

When injected into a peripheral vein (e.g., arm or hand vein), the microemulsion would be designed in a manner that it may or may not release the lipophilic drug that it is holding until it enters the central blood circulation. Using this design approach, patient safety and comfort would be markedly improved. Specifically, the damage and/or pain associated with peripheral intravenous injection for certain drugs such as chemotherapeutic agents and propofol could be significantly reduced or even eliminated. This technique may avoid the risks of placing a catheter into the central circulation to administer these types of drugs.

Figure 1:
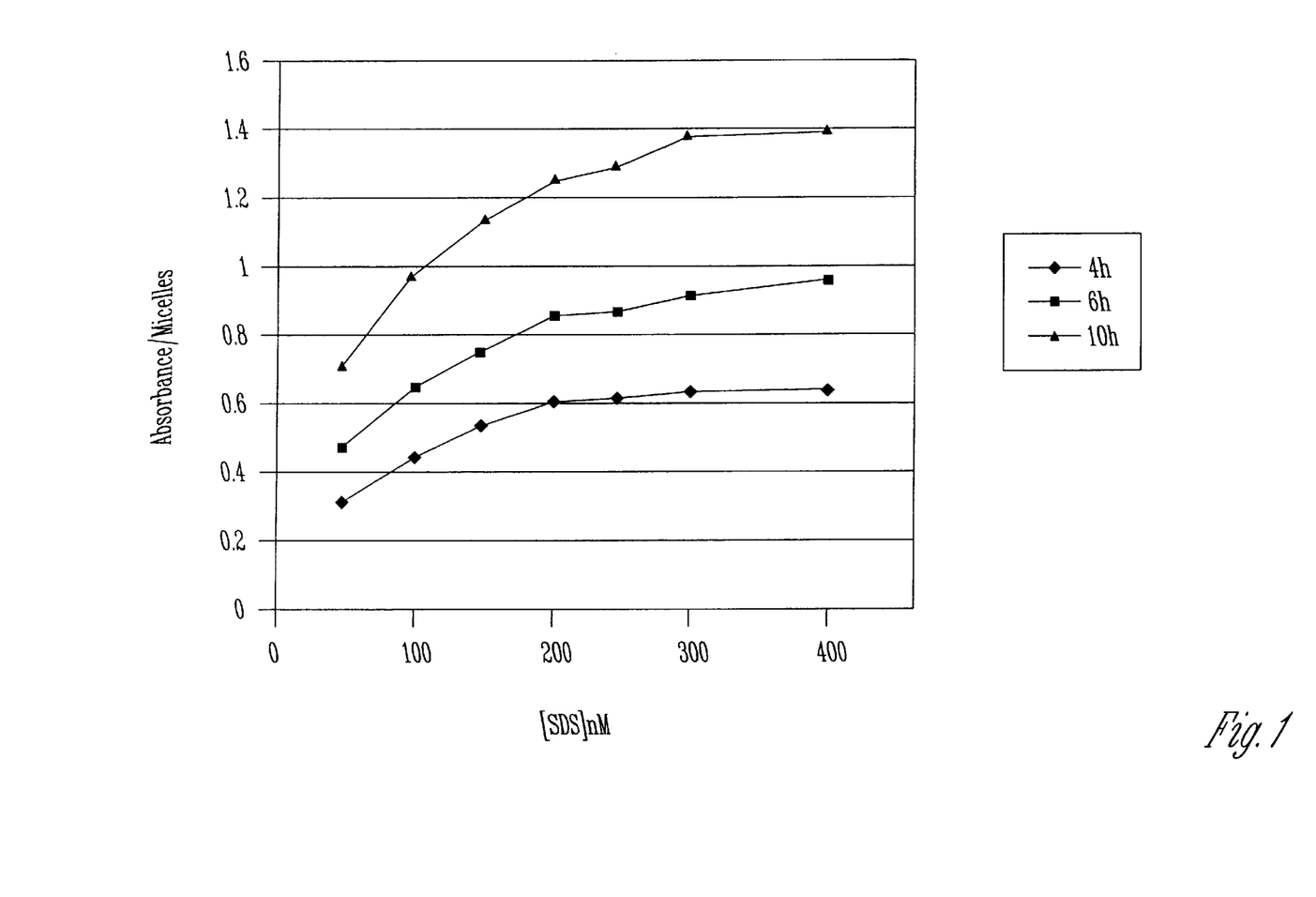
FIG. 1 shows release of active drug from microemulsions or micelles to Heptane phase.

Further modification of this approach can also be made so that one can tailor a micelle of a bio-compatible surfactant having definite stability or lifetime (milliseconds to hours). Solubility of these drugs and transfer to the surrounding medium is significantly influenced by the lifetime and, hence stability of the micelles. Experimental techniques are available to scientifically measure the stability of micelles from $10^{-3}$–$10^3$ seconds range. One can then correlate micellar stability and drug release rate. Such studies can be performed using the Franz diffusion cell wherein hairless mouse skin serves as a diffusion barrier between the donor and receptor cell compartments. In the donor compartment, micelles are placed with a specific relaxation time (i.e., lifetime or stability). A given drug's transfer rate into the receptor compartment can be measured and correlated to the stability of the micelles and drug release rate. Recently, we have performed similar studies using nonpolar dye molecules that were solubilized in micelles into the aqueous phase (FIG. 1).

Micelle stability significantly affects transfer rate of drugs. For example, one might deliver a long-acting, peripheral neural blockade using lidocaine instead of bupivicaine by encasing lidocaine in micelles with life spans of several hours. Because the therapeutic index for cardiotoxic effects of lidocaine is much greater than that for bupivicaine, use of tailored micelles would significantly enhance patient safety. (Therapeutic index is a pharmacological term regarding the margin of safety to be expected for a certain concentration of a drug to produce a desired effect [e.g., $TD_{50}$] compared to the concentration that causes an undesired effect [e.g., $LD_{50}$]) . Similarly, long-lived micelles might be useful for coating drug particles or viruses for permeation through the blood/brain barrier.

The following examples are further offered to illustrate but not limit the invention. In the examples herein, propofol was used as the drug selected. Propofol was used with a microemulsion emulsifier combination of Pluronic® F77 and sodium laurate in amounts specified below. Microemulsions with the emulsifier combination saline and propofol were made. Stability and viscosity were determined, using conventional methods and tabulated in Tables 1, 2, 3 and 4 below.

TABLE 1

Formulation parameters of propofol microemulsions
Total volume = 100 ml

| Sample Number | Pluronic F-77 (gm) | Sodium laurate (gm) | Propofol (ml) |
|---|---|---|---|
| 1A | 4.0 | — | — |
| 2A | 4.0 | — | 1.0 |
| 3A | 4.0 | 0.05 | 1.0 |
| 4A | 4.0 | 0.10 | 1.0 |
| 5A | 4.0 | 0.15 | 1.0 |
| 1B | 4.5 | — | — |
| 2B | 4.5 | — | 1.0 |
| 3B | 4.5 | 0.05 | 1.0 |
| 4B | 4.5 | 0.10 | 1.0 |
| 5B | 4.5 | 0.15 | 1.0 |

TABLE 2

The effect of temperature, and sodium laurate concentration and storage time on droplet size of propofol microemulsions.

| | Particle Size (nm) Freshly prepared (A) | | Particle Size (nm) 2 weeks later (B) | | Particle Size (nm) 5 months later (C) | |
|---|---|---|---|---|---|---|
| Age | 25° C. | 37° C. | 25° C. | 37° C. | 25° C. | 37° C. |
| 1A | — | — | — | — | — | — |
| 2A | 93.4 | 35.5 | 96.4 | 36.2 | 104.3 | 39.1 |
| 3A | 29.8 | 28.1 | 30.9 | 28.7 | 33.5 | 30.1 |
| 4A | 29.3 | 26.9 | 30.4 | 28.2 | 31.5 | 29.0 |

TABLE 2-continued

The effect of temperature, and sodium laurate concentration and storage time on droplet size of propofol microemulsions.

| | Particle Size (nm) Freshly prepared (A) | | Particle Size (nm) 2 weeks later (B) | | Particle Size (nm) 5 months later (C) | |
|---|---|---|---|---|---|---|
| Age | 25° C. | 37° C. | 25° C. | 37° C. | 25° C. | 37° C. |
| 5A | 25.1 | 24.2 | 25.7 | 25.1 | 25.3 | 25.1 |
| 1B | — | — | — | — | — | — |
| 2B | 72.1 | 32.8 | 78.7 | 35.8 | 85.6 | 38.3 |
| 3B | 29.3 | 27.4 | 29.7 | 27.7 | 30.5 | 28.3 |
| 4B | 26.9 | 25.1 | 27.4 | 25.6 | 27.4 | 25.8 |
| 5B | 24.6 | 24.1 | 24.7 | 24.3 | 24.9 | 24.7 |

TABLE 3

The effect of temperature, and sodium laurate concentration and storage time on pH level of propofol microemulsions

| | pH Freshly prepared (A) | | pH 2 weeks later (B) | | pH 5 months later (C) | |
|---|---|---|---|---|---|---|
| Age | 25° C. | 37° C. | 25° C. | 37° C. | 25° C. | 37° C. |
| Pf 77-1 | 6.58 | 6.58 | 6.55 | 6.52 | 6.5 | 6.5 |
| Pf 77-2 | 6.42 | 6.43 | 6.37 | 6.34 | 6.34 | 6.36 |
| Pf 77-3 | 7.32 | 7.3 | 7.11 | 7.08 | 7.14 | 7.06 |
| Pf 77-4 | 7.53 | 4.5 | 7.42 | 7.24 | 7.38 | 7.24 |
| Pf 77-5 | 7.62 | 7.66 | 7.58 | 7.4 | 7.52 | 7.42 |
| Pf 77-1 | 6.59 | 6.58 | 6.5 | 6.48 | 6.5 | 6.52 |
| Pf 77-2 | 6.42 | 6.41 | 6.34 | 6.30 | 6.36 | 6.3 |
| Pf 77-3 | 7.44 | 7.38 | 7.24 | 7.32 | 7.28 | 7.34 |
| Pf 77-4 | 7.57 | 7.54 | 7.46 | 7.5 | 7.5 | 7.52 |
| Pf 77-5 | 7.6 | 7.62 | 7.56 | 7.58 | 7.55 | 7.55 |

TABLE 4-A

The effect of temperature and shear rate on viscosity of freshly prepared propofol microemulsions

| Code of Emulsion | Viscosity in cps 10 S$^{-1}$ 25° C. | Viscosity in cps 10 S$^{-1}$ 37° C. | Viscosity in cps 100 S$^{-1}$ 25° C. | Viscosity in cps 100 S$^{-1}$ 37° C. | Viscosity in cps 1000 S$^{-1}$ 25° C. | Viscosity in cps 1000 S$^{-1}$ 37° C. |
|---|---|---|---|---|---|---|
| 1A | 1.77 | 1.57 | 1.73 | 1.27 | 1.73 | 1.26 |
| 2A | 53.45 | 33.45 | 13.20 | 1.26 | 5.14 | 4.66 |
| 3A | 2.22 | 1.49 | 1.94 | 1.255 | 1.77 | 1.21 |
| 4A | 2.18 | 1.33 | 1.81 | 1.20 | 1.71 | 1.20 |
| 5A | 1.66 | 1.34 | 1.64 | 1.24 | 1.635 | 1.205 |
| 1B | 1.75 | 1.59 | 1.81 | 1.35 | 1.80 | 1.36 |
| 2B | 13.2 | 1.44 | 6.37 | 1.31 | 3.46 | 1.28 |
| 3B | 2.04 | 1.51 | 1.87 | 1.33 | 1.79 | 1.30 |
| 4B | 1.85 | 1.41 | 1.80 | 1.30 | 1.77 | 1.29 |
| 5B | 1.43 | 1.21 | 1.58 | 1.22 | 1.47 | 1.206 |

TABLE 4-B

The effect of temperature and shear rate on viscosity of two week old propofol microemulsions

| Code of Emulsion | Viscosity in cps 10 S$^{-1}$ 25° C. | Viscosity in cps 10 S$^{-1}$ 37° C. | Viscosity in cps 100 S$^{-1}$ 25° C. | Viscosity in cps 100 S$^{-1}$ 37° C. | Viscosity in cps 1000 S$^{-1}$ 25° C. | Viscosity in cps 1000 S$^{-1}$ 37° C. |
|---|---|---|---|---|---|---|
| 1A | 1.77 | 1.57 | 1.73 | 1.275 | 1.73 | 1.29 |
| 2A | 59.5 | 20.95 | 14.3 | 10.4 | 5.52 | 4.39 |

TABLE 4-B-continued

The effect of temperature and shear rate on
viscosity of two week old propofol microemulsions

| Code of Emulsion | Viscosity in cps 10 $S^{-1}$ 25° C. | Viscosity in cps 10 $S^{-1}$ 37° C. | Viscosity in cps 100 $S^{-1}$ 25° C. | Viscosity in cps 100 $S^{-1}$ 37° C. | Viscosity in cps 1000 $S^{-1}$ 25° C. | Viscosity in cps 1000 $S^{-1}$ 37° C. |
|---|---|---|---|---|---|---|
| 3A | 3.13 | 1.66 | 2.37 | 1.24 | 1.97 | 1.20 |
| 4A | 2.51 | 1.34 | 1.91 | 1.21 | 1.75 | 1.22 |
| 5A | 1.69 | 1.51 | 1.62 | 1.23 | 1.63 | 1.23 |
| 1B | 1.74 | 1.63 | 1.80 | 1.35 | 1.81 | 1.35 |
| 2B | 13.0 | 1.49 | 6.36 | 1.40 | 3.47 | 1.35 |
| 3B | 2.06 | 1.69 | 1.91 | 1.33 | 1.91 | 1.32 |
| 4B | 1.86 | 1.51 | 1.81 | 1.29 | 1.79 | 1.27 |
| 5B | — | — | — | — | — | — |

TABLE 4-C

The effect of temperature and shear rate on
viscosity of five month old propofol microemulsions

| Code of Emulsion | Viscosity in cps 10 $S^{-1}$ 25° C. | Viscosity in cps 10 $S^{-1}$ 37° C. | Viscosity in cps 100 $S^{-1}$ 25° C. | Viscosity in cps 100 $S^{-1}$ 37° C. | Viscosity in cps 1000 $S^{-1}$ 25° C. | Viscosity in cps 1000 $S^{-1}$ 37° C. |
|---|---|---|---|---|---|---|
| 1A | 1.78 | 1.590 | 1.70 | 1.278 | 1.72 | 1.280 |
| 2A | 60.04 | 21.55 | 14.6 | 10.70 | 5.70 | 4.52 |
| 3A | 3.30 | 1.77 | 2.46 | 1.324 | 2.13 | 1.28 |
| 4A | 2.58 | 1.388 | 1.97 | 1.25 | 1.79 | 1.25 |
| 5A | 1.66 | 1.534 | 1.59 | 1.249 | 1.60 | 1.245 |
| 1B | 1.73 | 1.55 | 1.86 | 1.308 | 1.82 | 1.374 |
| 2B | 13.9 | 1.514 | 6.64 | 1.512 | 3.64 | 1.450 |
| 3B | 2.04 | 1.71 | 1.96 | 1.365 | 1.87 | 1.350 |
| 4B | 1.90 | 1.55 | 1.86 | 1.308 | 1.84 | 1.280 |
| 5B | — | — | — | — | — | — |

Figure 2:
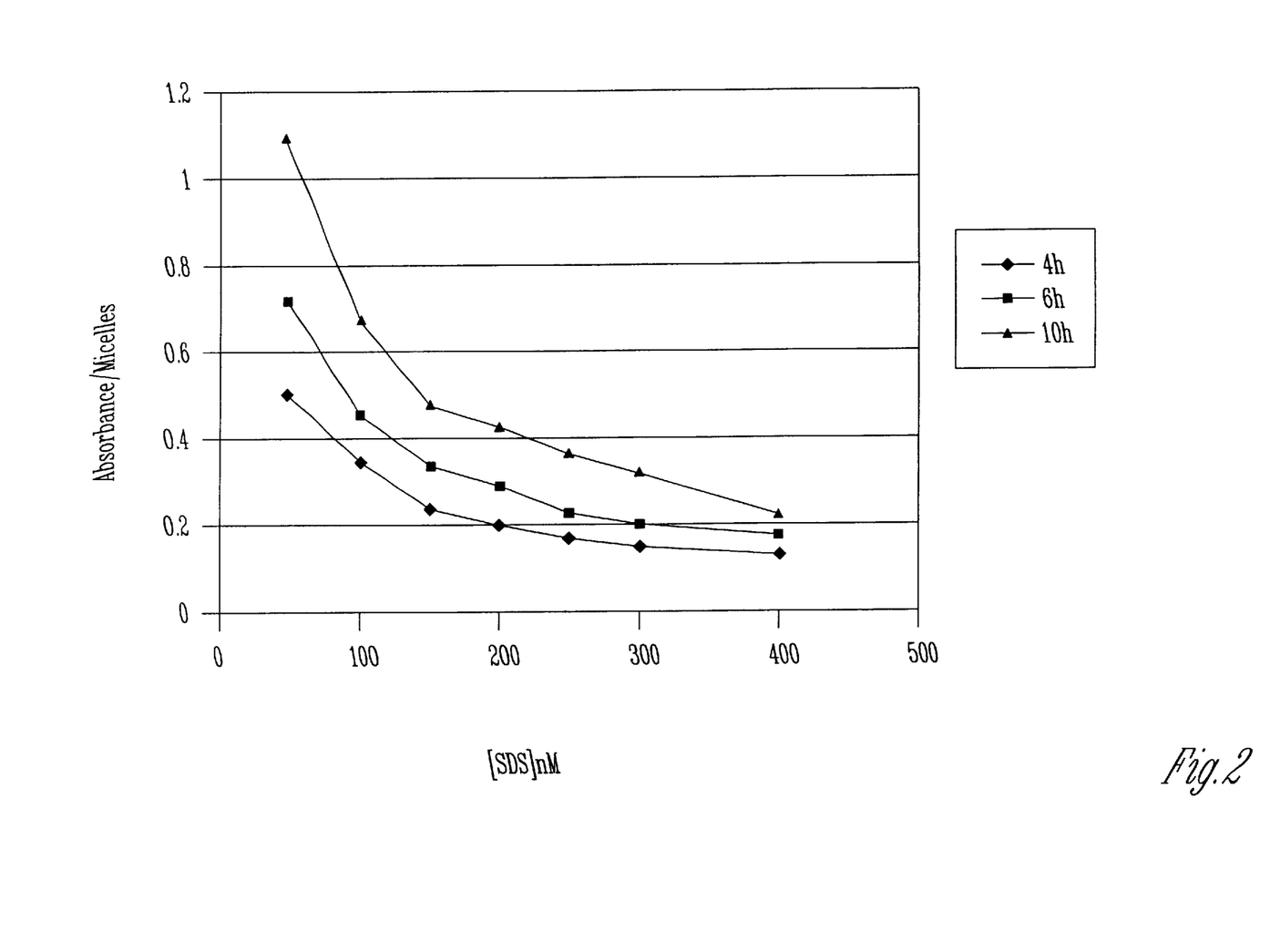
FIG. 2 shows similar experimental results.

Release from microemulsion micelles of the dye orange OT, using the co-emulsion combination of pluronic 77 and sodium laurate, are illustrated at 4, 6 and 10 hours respectively in FIGS. 1 and 2. As can be seen, the release rate is influenced by the micelles.

The anesthetic properties of propofol as a microemulsion in 0.9% normal saline (NS) with a Pluronic acid emulsifier were compared to those of propofol as a macroemulsion in Intralipid (Diprivan®) using a randomized, crossover design in a rat model for intravenous anesthetic induction and recovery.

This protocol was approved by the Animal Care and Use Committee of the University of Florida. Intravenous catheters (24 g) were inserted and secured in tail veins of Harlan Sprague-Dawley rats (350 g). Catheters were maintained with a cap and flushed with heparinized saline. Subsequently, rats were randomly administered either propofol/NS/Pluronic F-77 (University of Florida) after filtration through a 0.20 μm filter or sterile propofol/Intralipid (Diprivan®, AstraZeneca Pharmaceuticals, Inc., Wilmington, Del.) at a rate of 10 mg/kg/min. To remove the variability associated with the rate of injection caused by manual bolus administration and its effect on the rate of anesthetic induction, a syringe pump (sp2000i, World Precision Instruments, Sarasota, Fla.) was used to assure a constant rate of drug administration. Body temperature was maintained using a heating blanket (TP-400, Gaymar Industries, Inc., Orchard Park, N.Y.). The endpoint of anesthetic induction was total drug dose to cause the loss of reflexive withdrawal of the leg following a left great toe pinch. Following loss of withdrawal, the drug infusion was discontinued. Endpoints of anesthetic recovery were timed until recovery of spontaneous eye blinking, sustained head lift, and righting reflex. Following the first anesthetic and recovery, rats were allowed to fully recover for approximately 45 min. before receiving the alternative formulation of propofol. Rats were observed for seven days after receiving anesthesia.

All rats in both study groups experienced rapid induction of anesthesia with subsequent recovery. Continuous spontaneous ventilation occurred in every case. All rats maintained pink paws and ears. No rat died during seven days of observation after the anesthetic. Specific endpoints are detailed in Table 5.

TABLE 5

Anesthetic induction and recovery properties of
either propofol in a microemulsion using
NS/Pluronic F-77 or propofol in a macroemulsion of
Intralipid (Diprivan ®) in rats.

| Parameter | Propofol/NS/Pluronic F-77 Microemulsion | Propofol/Intralipid Macroemulsion | P value[a] |
|---|---|---|---|
| Total propofol dose (mg/kg) | 17.5 ± 2.2 | 14.9 ± 1.4 | 0.354 |
| Time to eye blinking (sec) | 609 ± 86 | 802 ± 57 | 0.184 |

TABLE 5-continued

Anesthetic induction and recovery properties of
either propofol in a microemulsion using
NS/Pluronic F-77 or propofol in a macroemulsion of
Intralipid (Diprivan ®) in rats.

| Parameter | Propofol/NS/Pluronic F-77 Microemulsion | Propofol/Intralipid Macroemulsion | P value[a] |
|---|---|---|---|
| Time to head lift (sec) | 691 ± 98 | 827 ± 63 | 0.459 |
| Time to righting (sec) | 756 ± 97 | 895 ± 34 | 0.393 |

Data expressed as mean ± SEM of three experiments.
[a]:2-tailed, paired t-test.

Based on these limited observations in a rat model, the anesthetic properties of propofol in a NS/Pluronic F-77 microemulsion formulation are at least equivalent to those of the commercially available propofol preparation, Diprivan®.

From the above it can be seen that the invention accomplishes at least all of its stated objectives. And, an important aspect of which is the combination emulsifier system of a long chain polymer surfactant component, and a short chain fatty acid component which set up a competitive adsorption at the interface of the oil and water to reduce interfacial tension to a very low value. This allows the formation of stable microemulsions, particularly so with the preferred drug propofol and the preferred emulsifier combination pluronic F77 and sodium laurate. The formed microemulsion is clear, not milky appearing at all times.

It, of course, goes without saying that certain modifications of the emulsification system can be made without departing from the spirit and scope of the present invention.

What is claimed is:

1. A microemulsion drug composition for intravenous delivery comprising:
   an oil phase consisting essentially of at least one drug;
   a long chain polymer surfactant component; and
   a short chain fatty acid surfactant component; and
   an aqueous phase,
   wherein the amounts of the long chain polymer and short chain fatty acid surfactant components are selected to provide for spontaneous formation of thermodynamically stable microemulsion droplets of the oil phase having a particle size from 10 nm to 100 nm and wherein the interfacial tension of the drug with said emulsifier combination is less than 0.1 dynes per cm.

2. The drug composition of claim 1 wherein the long chain polymer surfactant component is selected from the group consisting of polyoxyethylene alkyl esters, polyoxyethylene glycols; polyvinylpyrrolidone; polyvinylalcohol, tyloxapol, and poloxamer.

3. The drug composition of claim 2 wherein the long chain polymer surfactant component is a poloxamer.

4. The drug composition of claim 1 wherein the short chain fatty acid component is a $C_8$ to $C_{16}$ component.

5. The drug composition of claim 4 wherein the short chain fatty acid component is a $C_8$ to $C_{12}$ component.

6. The drug composition of claim 1 wherein the long chain surfactant component is a poloxamer and the fatty acid component is a laurate.

7. The drug composition of claim 1 wherein the drug is an oil.

8. The drug composition of claim 1 wherein the drug is selected from the group consisting of analgesics, anesthetics, antibiotics, antidepressants, antidiabetics, antifungals, antihypertensives, anti-inflammatories, antineoplastics, immunosuppressives, sedatives, antianginals, antipsychotics, antimanics, antiarthritics, antigouts, anticoagulants, antithrombolytics, anticonvulsants, antiparkinsons, antibacterials, antivirals, and anti-infectives.

9. The drug composition of claim 8 wherein the drug is an anesthetic.

10. The drug composition of claim 9 wherein the drug is an aryl.

11. The drug composition of claim 10 wherein the drug is propofol.

12. The drug composition of claim 1 wherein the ratio of long chain polymeric component to short chain fatty acid component is from 10 to 100 to 25 to 80 (wt/wt).

13. The drug composition of claim 1 wherein the long chain polymeric component has a molecular weight greater than 1000, and the short chain fatty acid component has a molecular weight less than 1000.

14. The drug composition of claim 12 wherein the amount of drug is from 0.1% to 1.0%.

15. The drug composition of claim 1 wherein the microemulsion is selected from the group consisting of oil-in-water, water-in-oil and interphase emulsions.

16. The drug composition of claim 1 wherein the drug is a mixture of the base form and the salt form of the drug.

17. The drug composition of claim 1, wherein the drug transfer rate is controlled by control of the character and nature of micelle formation of the microemulsion.

18. A method of controlling intravenous drug delivery and transfer rate of drugs comprising:
   preparing microdroplets of the drug with an emulsifier combination of a long chain polymer surfactant component, and a short chain fatty acid surfactant component, the amounts of each being selected to provide for spontaneous formation of thermodynamically stable microemulsion droplets and to control intravenous delivery and transfer rate as desired,
   wherein the drug interfacial tension with the emulsion is less than 0.1 dynes per cm with a droplet size of the active drug in the carrier being less than 100 nm.

19. The drug composition of claim 1, wherein the total amount of surfactant components does not exceed 4.65% by weight.

20. The method of claim 18, wherein the total amount of surfactant does not exceed 4.65% by weight.

* * * * *